United States Patent
Dakka et al.

(10) Patent No.: US 9,452,965 B2
(45) Date of Patent: Sep. 27, 2016

(54) PROCESS FOR PRODUCING PHENOL AND/OR CYCLOHEXANONE FROM CYCLOHEXYLBENZENE

(71) Applicant: ExxonMobil Chemical Patents Inc., Baytown, TX (US)

(72) Inventors: Jihad M. Dakka, Whitehouse Station, NJ (US); Charles Morris Smith, Princeton, NJ (US); Keith H. Kuechler, Friendswood, TX (US); Christopher L. Becker, Manhattan, KS (US); Terry E. Helton, Montgomery, TX (US); Jason D. Davis, Humble, TX (US); Edmund J. Mozeleski, Somerset, NJ (US)

(73) Assignee: ExxonMobil Chemical Patents Inc., Baytown, TX (US)

( * ) Notice: Subject to any disclaimer, the term of this patent is extended or adjusted under 35 U.S.C. 154(b) by 0 days.

(21) Appl. No.: 14/421,746

(22) PCT Filed: Sep. 13, 2013

(86) PCT No.: PCT/US2013/059672
§ 371 (c)(1),
(2) Date: Feb. 13, 2015

(87) PCT Pub. No.: WO2014/043478
PCT Pub. Date: Mar. 20, 2014

(65) Prior Publication Data
US 2015/0218074 A1   Aug. 6, 2015

Related U.S. Application Data

(60) Provisional application No. 61/701,997, filed on Sep. 17, 2012.

(30) Foreign Application Priority Data

Nov. 19, 2012 (EP) .................................... 12193132

(51) Int. Cl.
| | |
|---|---|
| C07C 45/00 | (2006.01) |
| C07C 45/53 | (2006.01) |
| C07C 37/08 | (2006.01) |
| C07C 1/24 | (2006.01) |
| C07C 2/74 | (2006.01) |
| C07C 5/03 | (2006.01) |
| C07C 407/00 | (2006.01) |
| B01J 29/08 | (2006.01) |
| C07C 2/66 | (2006.01) |
| C07C 5/05 | (2006.01) |

(52) U.S. Cl.
CPC ............... *C07C 45/53* (2013.01); *B01J 29/08* (2013.01); *C07C 1/24* (2013.01); *C07C 2/66* (2013.01); *C07C 2/74* (2013.01); *C07C 5/03* (2013.01); *C07C 5/05* (2013.01); *C07C 37/08* (2013.01); *C07C 407/00* (2013.01); *C07C 2101/14* (2013.01); *C07C 2101/16* (2013.01); *C07C 2529/70* (2013.01)

(58) Field of Classification Search
CPC ........... C07C 1/24; C07C 45/53; B01J 29/08
USPC ........................................................ 568/342
See application file for complete search history.

(56) References Cited

U.S. PATENT DOCUMENTS

| | | | |
|---|---|---|---|
| 6,037,513 A * | 3/2000 | Chang | B01J 29/72 585/268 |
| 6,720,462 B2 | 4/2004 | Kuhnle et al. | |
| 6,852,893 B2 | 2/2005 | Kuhnle et al. | |
| 7,446,232 B2 | 11/2008 | Dakka et al. | |
| 8,461,398 B2 | 6/2013 | Dakka et al. | |
| 8,791,306 B2 | 7/2014 | Dakka et al. | |
| 2002/0169331 A1 | 11/2002 | Miura et al. | |
| 2007/0265476 A1 | 11/2007 | Dakka et al. | |
| 2008/0086018 A1 | 4/2008 | Cheng et al. | |
| 2008/0154082 A1 | 6/2008 | Dandekar et al. | |
| 2009/0187047 A1 | 7/2009 | Dakka et al. | |
| 2009/0306433 A1 | 12/2009 | Dakka et al. | |
| 2009/0312580 A1 | 12/2009 | Cheng et al. | |
| 2011/0190543 A1 | 8/2011 | Dakka et al. | |

FOREIGN PATENT DOCUMENTS

| | | | |
|---|---|---|---|
| CN | 1962574 | 5/2007 | |
| EP | 1074536 | 5/2005 | |
| WO | WO2006/015825 | 2/2006 | |
| WO | WO2007/093357 | 8/2007 | |
| WO | WO2007/093359 | 8/2007 | |
| WO | WO2008/101616 | 8/2008 | |
| WO | WO2009/131769 | 10/2009 | |
| WO | WO 2009131769 A1 * | 10/2009 | ............ B01J 29/064 |
| WO | WO2010/098916 | 9/2010 | |
| WO | WO2014/043188 | 3/2014 | |

* cited by examiner

OTHER PUBLICATIONS

International Search Report; PCT/US2013/059672.*

*Primary Examiner* — Porfirio Nazario Gonzalez
*Assistant Examiner* — Kofi Adzamli
(74) *Attorney, Agent, or Firm* — Stephen A. Baehl

(57) ABSTRACT

A process for producing phenol and/or cyclohexanone is described in which cyclohexylbenzene is contacted with an oxygen-containing gas under conditions effective to produce an oxidation effluent comprising cyclohexylbenzene hydroperoxide and at least part of cyclohexylbenzene hydroperoxide is contacted with a cleavage catalyst under conditions effective to produce a cleavage effluent containing phenol and cyclohexanone. At least one of the oxidation effluent and the cleavage effluent contains at least one phenylcyclohexanol as a by-product and the process further comprises contacting the phenylcyclohexanol with a dehydration catalyst comprising a molecular sieve of the MCM-22 family under conditions effective to convert at least part of the phenylcyclohexanol to phenylcyclohexene.

25 Claims, 6 Drawing Sheets

PROCESS FOR PRODUCING PHENOL AND/OR CYCLOHEXANONE FROM CYCLOHEXYLBENZENE

PRIORITY CLAIM

This application is a National Stage Application of International Application No. PCT/US2013/059672, filed Sep. 13, 2013, which claims the benefit of U.S. Provisional Application No. 61/701,997, filed Sep. 17, 2012, and European Application No. 12193132.3, filed Nov. 19, 2012, the disclosures of which are fully incorporated herein by their reference.

FIELD

The present invention relates to a process for producing phenol.

BACKGROUND

Phenol is an important product in the chemical industry and is useful in, for example, the production of phenolic resins, bisphenol A, ε-caprolactam, adipic acid, and plasticizers.

Currently, the most common route for the production of phenol is the Hock process via cumene. This is a three-step process in which the first step involves alkylation of benzene with propylene in the presence of an acidic catalyst to produce cumene. The second step is oxidation, preferably aerobic oxidation, of the cumene to the corresponding cumene hydroperoxide. The third step is the cleavage of the cumene hydroperoxide in the presence of heterogeneous or homogenous catalysts into equimolar amounts of phenol and acetone, a co-product. However, the world demand for phenol is growing more rapidly than that for the acetone co-product. In addition, due to developing shortages in supply, the cost of propylene is likely to increase.

Thus, a process that avoids or reduces the use of propylene as a feed and coproduces higher ketones, rather than acetone, may be an attractive alternative route to the production of phenol. For example, there is a growing market for cyclohexanone, which is used as an industrial solvent, as an activator in oxidation reactions and in the production of adipic acid, cyclohexanone resins, cyclohexanone oxime, caprolactam, and nylon 6.

It is known that phenol and cyclohexanone can be co-produced by a variation of the Hock process in which cyclohexylbenzene is oxidized to obtain cyclohexylbenzene hydroperoxide and the hydroperoxide is decomposed in the presence of an acid catalyst to the desired phenol and cyclohexanone. Although various methods are available for the production of cyclohexylbenzene, a preferred route is via benzene hydroalkylation in which benzene is contacted with hydrogen in the presence of a catalyst such that part of the benzene is converted into cyclohexene which then reacts with the remaining benzene to produce the desired cyclohexylbenzene. One such method is disclosed in U.S. Pat. No. 6,037,513, in which the catalyst comprises a molecular sieve of the MCM-22 family and at least one hydrogenation metal selected from palladium, ruthenium, nickel, cobalt, and mixtures thereof. The '513 patent also discloses that the resultant cyclohexylbenzene can be oxidized to the corresponding hydroperoxide which is then decomposed to the desired phenol and cyclohexanone co-product in roughly equimolar amounts.

However, non-negligible amounts of by-products, including phenylcyclohexanols, are generated during the oxidation and/or cleavage steps. To improve product yields, these by-products are preferably converted to cyclohexylbenzene by a two stage process involving dehydration followed by hydrogenation. However, the catalysts and conversion conditions suitable for effecting the dehydration reaction are also prone to driving potential side reactions of the phenylcyclohexene intermediates as well as any residual cyclohexylbenzene or desired product (cyclohexanone and phenol) that may be present in the dehydration feed. Thus, cyclohexanone can undergo aldol condensation to heavy products and phenol can be alkylated with phenylcyclohexene and cyclohexylbenzene. In addition, the phenylcyclohexene intermediate can undergo reactions such as dimerization, alkylation with residual cyclohexylbenzene, isomerization to other products, such as methylcyclopentylbenzene, and hydride transfer to biphenyl. Not only do these side reactions involve potential loss of valuable product, but they can also lead to deactivation of the dehydration catalyst.

SUMMARY

It has now been found that molecular sieves of MCM-22 family are uniquely active, stable and selective for the dehydration of the phenylcyclohexanols produced as by-products of cyclohexylbenzene oxidation and cleavage. The phenylcyclohexene produced by the dehydration reaction can then be hydrogenated to cyclohexylbenzene for recycle to the oxidation step.

In one aspect, the invention resides in a process for producing phenol and/or cyclohexanone, said process comprising:
(a) contacting cyclohexylbenzene with an oxygen-containing gas under conditions effective to produce an oxidation effluent containing cyclohexylbenzene hydroperoxide;
(b) contacting at least part of said oxidation effluent containing cyclohexylbenzene hydroperoxide with a cleavage catalyst under conditions effective to produce a cleavage effluent containing phenol and cyclohexanone,
wherein at least one of said oxidation effluent and said cleavage effluent contains at least one phenylcyclohexanol as a by-product; and
(c) contacting at least part of said at least one effluent containing said at least one phenylcyclohexanol with a dehydration catalyst comprising a molecular sieve of the MCM-22 family under conditions effective to convert at least part of said phenylcyclohexanol to phenylcyclohexene.

In certain embodiments, the at least one by-product comprises one or more of 2-phenyl-1-cyclohexanol, 3-phenyl-1-cyclohexanol, and 4-phenyl-1-cyclohexanol.

In one embodiment, the molecular sieve of the MCM-22 family comprises MCM-56 and the conditions in said contacting step (c) comprise a temperature of 25° C. to 200° C.

In certain embodiments, the process further comprises:
(d) contacting at least part of the phenylcyclohexene produced in said contacting step (c) with hydrogen under conditions effective to convert at least part of said phenylcyclohexene to cyclohexylbenzene.

Desirably, the conditions in said contacting step (d) comprise a temperature of 80° C. to 150° C. and a hydrogen partial pressure of 15 kPa to 1000 kPa. Said contacting steps (c) and (d) are desirably conducted in separate reaction zones.

In one embodiment, the process further comprises:

(e) separating at least part of said cleavage effluent from said contacting step (b) into a first fraction containing phenol and cyclohexanone and a second fraction containing said at least one phenylcyclohexanol; and (f) supplying said second fraction to said contacting step (c).

In certain embodiments, at least part of the cyclohexylbenzene produced in said step (d) is recycled to said contacting step (a).

A second aspect of the invention resides in a process for producing phenol and/or cyclohexanone, said process comprising:

(I) contacting benzene with hydrogen in the presence of a hydroalkylation catalyst under an hydroalkylation condition effective to produce a hydroalkylation effluent comprising cyclohexylbenzene;

(II) contacting at least part of said cyclohexylbenzene in said hydroalkylation effluent with an oxygen-containing gas under conditions effective to produce an oxidation effluent containing cyclohexylbenzene hydroperoxide;

(III) contacting at least part of said oxidation effluent containing cyclohexylbenzene hydroperoxide with a cleavage catalyst under conditions effective to produce a cleavage effluent containing phenol and cyclohexanone, wherein at least one of said oxidation effluent and said cleavage effluent contains at least one phenylcyclohexanol; and (IV) contacting at least part of said at least one effluent containing said at least one phenylcyclohexanol with a dehydration catalyst comprising a molecular sieve of the MCM-22 family under conditions effective to convert at least part of said phenylcyclohexanol to phenylcyclohexene.

DETAILED DESCRIPTION OF THE EMBODIMENTS

Figure 1:
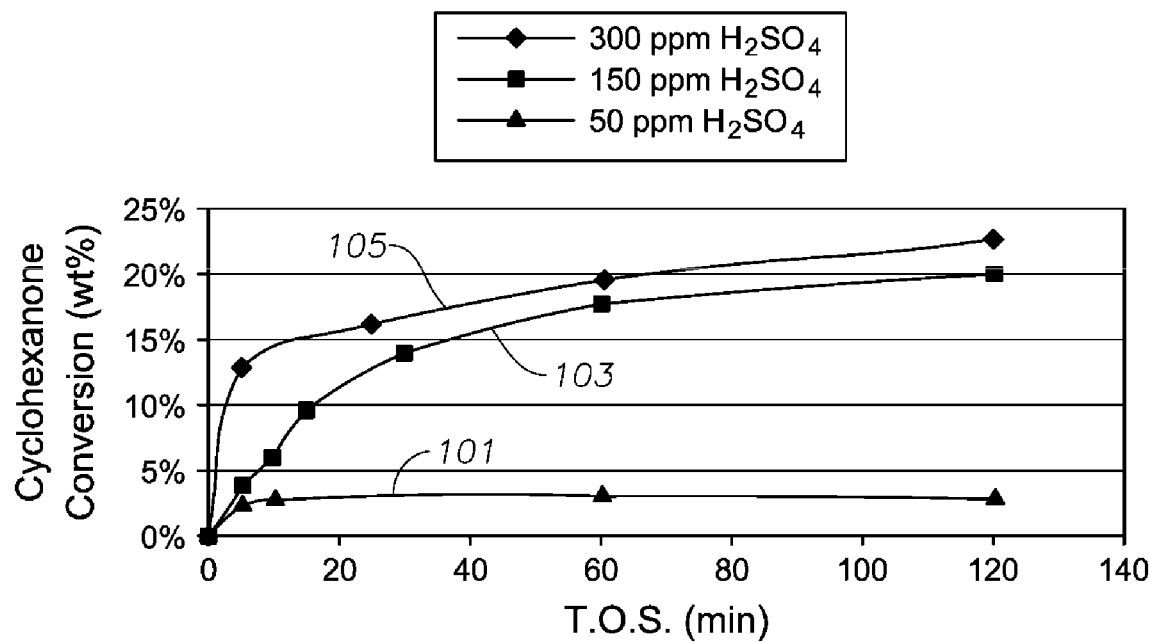
FIG. 1 is a graph comparing cyclohexanone conversion against time on stream for the different sulfuric acid concentrations used in the process of Example 1.

In the present disclosure, a process may be described as comprising at least one "step." It should be understood that each step is an action or operation that may be carried out once or multiple times in the process, in a continuous or discontinuous fashion. Unless specified to the contrary or the context clearly indicates otherwise, each step in a process may be conducted sequentially in the order as they are listed, with or without overlapping with one or more other step, or in any other order, as the case may be. In addition, some steps mat be conducted simultaneously, for example, in the same reaction zone.

Unless otherwise indicated, all numbers in the present disclosure are to be understood as being modified by the term "about" in all instances. It should also be understood that the precise numerical values used in the specification and claims constitute specific embodiments. Efforts have been made to ensure the accuracy of the data in the examples. However, it should be understood that any measured data inherently contains a certain level of error due to the limitation of the technique and equipment used for making the measurement.

As used herein, the indefinite article "a" or "an" shall mean "at least one" unless specified to the contrary or the context clearly indicates otherwise.

As used herein, the term "cyclohexylbenzene" shall mean benzene substituted by a single cyclohexyl group, unless specified to the contrary or the context clearly indicates otherwise. As used herein, the generic term "dicyclohexylbenzene" shall include 1,2-dicyclohexylbenzene, 1,3-dicyclohexylbenzne, 1,4-dicyclohexylbenzene, and mixtures and combinations of at least two thereof in any proportion. As used herein, the generic term "tricyclohexylbenzene" shall include 1,2,3-tricyclohexylbenzene, 1,2,4-tricyclohexylbenzene and 1,3,5-tricyclohexylbenzene, and combinations and mixtures thereof at any proportion. The generic term "polycycloyhexylbenzene" shall include any of the dicyclohexylbenzene isomers and tricyclohexylbenzene isomers described above, and combinations and mixtures of at least two thereof in any proportion.

A process is described herein for producing phenol and/or cyclohexanone from cyclohexylbenzene. In the process, cyclohexylbenzene is initially oxidized to produce cyclohexylbenzene hydroperoxide, which can then be cleaved to generate the desired phenol and cyclohexanone. However, the oxidation and cleavage steps also produce non-insignificant amounts of by-products, including phenylcyclohexanols, which are desirably present in the cleavage effluent in an amount from 0.1 wt % to 10 wt %, such as from 0.5 wt % to 5 wt %, of the effluent. In certain embodiments of the present process, the phenylcyclohexanol by-products are selectively converted over an MCM-56 catalyst to phenylcyclohexenes, either with or without prior separation of the by-products from the cleavage effluent. The phenylcyclohexenes can subsequently be hydrogenated to produce cyclohexylbenzene, which can then be recycled to the oxidation step.

In one preferred embodiment, the present process forms part of an integrated process for producing phenol from benzene in which the benzene is initially alkylated or hydroalkylated to produce the cyclohexylbenzene feed to the present process. The ensuing description will therefore focus on this integrated process.

Production of Cyclohexylbenzene

The cyclohexylbenzene starting material for the present process can be produced by the alkylation of benzene with cyclohexene according to the following reaction:

The cyclohexene can be supplied to the reaction zone as a separate feed from the benzene, but normally is produced in situ by the selective hydrogenation of benzene in the presence of a bifunctional catalyst. In the latter case where cyclohexene is produced in situ, the overall reaction is generally termed "hydroalkylation" and may be summarized as follows:

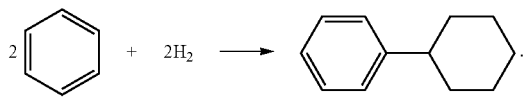

Any commercially available benzene feed can be used in the hydroalkylation step, but preferably the benzene has a purity level of at least 99 wt %. Similarly, although the source of hydrogen is not critical, it is desirable in certain embodiments that the hydrogen is at least 99 wt % pure.

Conveniently, the total feed to the hydroalkylation step contains less than 1000 ppm, such as less than 500 ppm, for example less than 100 ppm, water. In addition, the total feed desirably contains less than 100 ppm, such as less than 30 ppm, for example less than 3 ppm, sulfur and less than 10 ppm, such as less than 1 ppm, for example less than 0.1 ppm, nitrogen.

Hydrogen can be supplied to the hydroalkylation step over a wide range of values, but desirably is arranged such that the molar ratio of hydrogen to benzene in the hydroalkylation feed is from about 0.15:1 to about 15:1, such as from about 0.4:1 to about 4:1, for example from about 0.4 to about 0.9:1.

In addition to the benzene and hydrogen, a diluent, which is substantially inert under hydroalkylation conditions, may be supplied to the hydroalkylation reaction. Desirably the diluent is a hydrocarbon, in which the desired cycloalkylaromatic product, in this case cyclohexylbenzene, is soluble, such as a straight chain paraffinic hydrocarbon, a branched chain paraffinic hydrocarbon, and/or a cyclic paraffinic hydrocarbon. Examples of suitable diluents are decane and cyclohexane. Cyclohexane is a particularly attractive diluent since it is an unwanted by-product of the hydroalkylation reaction.

Although the amount of diluent is not narrowly defined, in certain embodiments the diluent is added in an amount such that the weight ratio of the diluent to the aromatic compound is at least 1:100, for example at least 1:10, but no more than 10:1, desirably no more than 4:1.

The hydroalkylation reaction can be conducted in a wide range of reactor configurations including fixed bed, slurry reactors, and/or catalytic distillation towers. In addition, the hydroalkylation reaction can be conducted in a single reaction zone or in a plurality of reaction zones, in which at least the hydrogen is introduced to the reaction in stages. Suitable reaction temperatures are from about 100° C. to about 400° C., such as from about 125° C. to about 250° C., while suitable reaction pressures are from about 100 kPa to about 7,000 kPa, such as from about 500 kPa to about 5,000 kPa.

The catalyst employed in the hydroalkylation reaction is a bifunctional catalyst comprising a hydrogenating metal component and an alkylating acid component (e.g., a solid acid component). In certain embodiments, the alkylating solid acid component comprises a molecular sieve of the MCM-22 family. The term "MCM-22 family material" (or "material of the MCM-22 family" or "molecular sieve of the MCM-22 family"), as used herein, includes one or more of:

molecular sieves made from a common first degree crystalline building block unit cell, which unit cell has the MWW framework topology. (A unit cell is a spatial arrangement of atoms which if tiled in three-dimensional space describes the crystal structure. Such crystal structures are discussed in the "Atlas of Zeolite Framework Types", Fifth edition, 2001, the entire content of which is incorporated as reference);

molecular sieves made from a common second degree building block, being a 2-dimensional tiling of such MWW framework topology unit cells, forming a monolayer of one unit cell thickness, preferably one c-unit cell thickness;

molecular sieves made from common second degree building blocks, being layers of one or more than one unit cell thickness, wherein the layer of more than one unit cell thickness is made from stacking, packing, or binding at least two monolayers of one unit cell thickness. The stacking of such second degree building blocks can be in a regular fashion, an irregular fashion, a random fashion, or any combination thereof; and molecular sieves made by any regular or random 2-dimensional or 3-dimensional combination of unit cells having the MWW framework topology.

Molecular sieves of MCM-22 family generally have an X-ray diffraction pattern including d-spacing maxima at 12.4±0.25, 6.9±0.15, 3.57±0.07, and 3.42±0.07 Angstrom. The X-ray diffraction data used to characterize the material are obtained by standard techniques using the K-alpha doublet of copper as the incident radiation and a diffractometer equipped with a scintillation counter and associated computer as the collection system. Molecular sieves of MCM-22 family include MCM-22 (described in U.S. Pat. No. 4,954,325), PSH-3 (described in U.S. Pat. No. 4,439,409), SSZ-25 (described in U.S. Pat. No. 4,826,667), ERB-1 (described in European Patent No. 0293032), ITQ-1 (described in U.S. Pat. No. 6,077,498), ITQ-2 (described in International Patent Publication No. WO97/17290), MCM-36 (described in U.S. Pat. No. 5,250,277), MCM-49 (described in U.S. Pat. No. 5,236,575), MCM-56 (described in U.S. Pat. No. 5,362,697), UZM-8 (described in U.S. Pat. No. 6,756,030), and mixtures thereof. Preferably, the molecular sieve is selected from (a) MCM-49; (b) MCM-56; and (c) isotypes of MCM-49 and MCM-56, such as ITQ-2.

Any known hydrogenating metal can be employed in the hydroalkylation catalyst, although suitable metals include palladium, ruthenium, nickel, zinc, tin, and cobalt, with palladium being particularly advantageous. In certain embodiments, the amount of hydrogenating metal present in the catalyst is from about 0.05 wt % to about 10 wt %, such as from about 0.1 wt % to about 5 wt %, of the catalyst. In one embodiment, where the MCM-22 family molecular sieve is an aluminosilicate, the amount of hydrogenating metal present is such that the molar ratio of the aluminum in the molecular sieve to the hydrogenating metal is from about 1.5 to about 1500, for example from about 75 to about 750, such as from about 100 to about 300.

The hydrogenating metal may be directly supported on the MCM-22 family molecular sieve by, for example, impregnation or ion exchange. However, in a more preferred embodiment, at least 50 wt %, for example at least 75 wt %, and in certain embodiments substantially all of the hydrogenating metal is supported on an inorganic oxide separate from but composited with the molecular sieve. In particular, it is found that by supporting the hydrogenating metal on the inorganic oxide, the activity of the catalyst and its selectivity to cyclohexylbenzene and dicyclohexylbenzene are increased as compared with an equivalent catalyst in which the hydrogenating metal is supported on the molecular sieve.

The inorganic oxide employed in such a composite hydroalkylation catalyst is not narrowly defined provided it is stable and inert under the conditions of the hydroalkylation reaction. Suitable inorganic oxides include oxides of Groups 2, 4, 13, and 14 of the Periodic Table of Elements, such as alumina, titania, and/or zirconia. As used herein, the numbering scheme for the Periodic Table Groups is as disclosed in Chemical and Engineering News, 63(5), 27 (1985).

The hydrogenating metal is deposited on the inorganic oxide, conveniently by impregnation, before the metal-containing inorganic oxide is composited with the molecular sieve. Desirably, the catalyst composite is produced by co-pelletization, in which a mixture of the molecular sieve and the metal-containing inorganic oxide are formed into pellets at high pressure (in certain embodiments about 350 kPa to about 350,000 kPa), or by co-extrusion, in which a slurry of the molecular sieve and the metal-containing inorganic oxide, optionally together with a separate binder, are forced through a die. If necessary, additional hydrogenating metal can subsequently be deposited on the resultant catalyst composite.

Although the hydroalkylation reaction using an MCM-22 family zeolite catalyst is highly selective towards cyclohexylbenzene, the effluent from the hydroalkylation reaction will likely contain some dicyclohexylbenzene by-product. Depending on the amount of this dicyclohexylbenzene, it may be desirable to either (a) transalkylate the dicyclohexylbenzene with additional benzene or (b) dealkylate the dicyclohexylbenzene to maximize the production of the desired monoalkylated species.

Transalkylation with additional benzene is desirably effected in a transalkylation reactor, separate from the hydroalkylation reactor, over a suitable transalkylation catalyst, such as a molecular sieve of the MCM-22 family, zeolite beta, MCM-68 (see U.S. Pat. No. 6,014,018), zeolite Y, and mordenite. The transalkylation reaction is desirably conducted under at least partial liquid phase conditions, which suitably include a temperature of about 100° C. to about 300° C., a pressure of about 800 kPa to about 3500 kPa, a weight hourly space velocity of about 1 $hr^{-1}$ to about 10 $hr^{-1}$ on total feed, and a benzene/dicyclohexylbenzene weight ratio of about 1:1 to about 5:1.

Dealkylation or cracking is also desirably effected in a reactor separate from the hydroalkylation reactor, such as a reactive distillation unit, at a temperature of about 150° C. to about 500° C. and a pressure of 15 psig to 500 psig (200 kPa to 3550 kPa) over an acid catalyst such as an aluminosilicate, a silicoaluminphosphate, amorphous silica-alumina, an acidic clay, a mixed metal oxide, such as $WO_x/ZrO_2$, phosphoric acid, sulfated zirconia, and mixtures thereof. In certain embodiments, the acid catalyst includes at least one aluminosilicate, aluminophosphate or silicoaluminphosphate of the FAU, AEL, AFI, and MWW structural types. Unlike transalkylation, dealkylation can be conducted in the absence of added benzene, although it may be desirable to add benzene to the dealkylation reaction to reduce coke formation. In this case, the weight ratio of benzene to poly-alkylated aromatic compounds in the feed to the dealkylation reaction is desirably from 0 to about 0.9, such as from about 0.01 to about 0.5. Similarly, although the dealkylation reaction can be conducted in the absence of added hydrogen, in certain embodiments, hydrogen is introduced into the dealkylation reactor to assist in coke reduction. Suitable hydrogen addition rates are such that the molar ratio of hydrogen to poly-alkylated aromatic compound in the total feed to the dealkylation reactor is from about 0.01 to about 10.

Another by-product of the hydroalkylation reaction is cyclohexane. Although a $C_6$-rich stream comprising cyclohexane and unreacted benzene can be readily removed from the hydroalkylation reaction effluent by distillation, owing to the similarity in the boiling points of benzene and cyclohexane, the $C_6$-rich stream is difficult to further separate by simple distillation. However, some or all of the $C_6$-rich stream can be recycled to the hydroalkylation reactor to provide not only part of the benzene feed, but also part of the diluents mentioned above.

In some cases, it may be desirable to supply some of the $C_6$-rich stream to a dehydrogenation reaction zone, where the $C_6$-rich stream is contacted with a dehydrogenation catalyst under dehydrogenation conditions sufficient to convert at least part of the cyclohexane in the $C_6$-rich stream portion to benzene, which again can be recycled to the hydroalkylation reaction. The dehydrogenation catalyst in certain embodiments comprises (a) a support; (b) a hydrogenation-dehydrogenation component; and (c) an inorganic promoter. Conveniently, the support (a) is selected from the group consisting of silica, a silicate, an aluminosilicate, zirconia, and carbon nanotubes, and preferably comprises silica. Suitable hydrogenation-dehydrogenation components (b) comprise at least one metal selected from Groups 6 to 10 of the Periodic Table of Elements, such as platinum, palladium, and compounds and mixtures thereof. Desirably, the hydrogenation-dehydrogenation component is present in an amount from about 0.1 wt % to about 10 wt % of the catalyst. A suitable inorganic promoter (c) comprises at least one metal or compound thereof selected from Group 1 of the Periodic Table of Elements, such as a potassium compound. Desirably, the promoter is present in an amount from about 0.1 wt % to about 5 wt % of the catalyst. Suitable dehydrogenation conditions include a temperature of about 250° C. to about 500° C., a pressure of about atmospheric to about 500 psig (100 kPa to 3550 kPa), a weight hourly space velocity of about 0.2 $hr^{-1}$ to 50 $hr^{-1}$, and a hydrogen to hydrocarbon feed molar ratio of about 0 to about 20.

Other disadvantageous impurities of the hydroalkylation reaction are bicyclohexyl (BCH) and the methylcyclopentylbenzene (MCPB) isomers which, because of the similarity in their boiling points, are difficult to separate from the desired cyclohexylbenzene by distillation. Moreover, although 1,2-methylcyclopentylbenzene (2-MCPB), and 1,3-methylcyclopentylbenzene (3-MCPB) are readily converted in the subsequent oxidation/cleavage steps to the phenol and methylcyclopentanones, which are valuable products, 1,1-methylcyclopentylbenzene (1-MCPB) is substantially inert to the oxidation step and so, if not removed, will build up in the $C_{12}$ stream. Similarly, bicyclohexyl (BCH) can lead to separation problems downstream. Thus, at least part of the hydroalkylation reaction product may be treated with a catalyst under conditions to remove at least 1,1-methylcyclopentylbenzene and/or bicyclohexyl from the product. The catalyst is desirably an acid catalyst, such as an aluminosilicate zeolite, and especially faujasite and the treatment is conducted at a temperature of about 100° C. to about 350° C., such as about 130° C. to about 250° C., for a time of about 0.1 to about 3 hours, such as about 0.1 to about 1 hour. The catalytic treatment is believed to isomerize the 1,1-methylcyclopentylbenzene to the more readily oxidizable 1,2-methylcyclopentylbenzene (2-MCPB), and 1,3-methylcyclopentylbenzene (3-MCPB). The bicyclohexyl is believed to react with benzene present in the hydroalkylation reaction product to produce cyclohexane and more of the desired cyclohexylbenzene according to the following reaction:

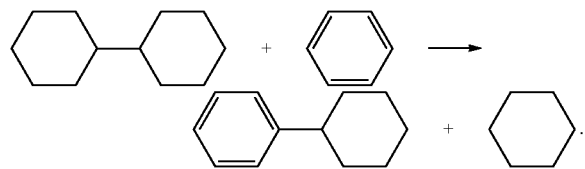

The catalytic treatment can be conducted on the direct product of the hydroalkylation reaction or after distillation of the hydroalkylation reaction product to separate the $C_6$ and/or the heavies fraction.

The cyclohexylbenzene product from the hydroalkylation reaction and any downstream reaction to remove the impurities discussed herein is separated from the reaction effluent(s) and is fed to the oxidation reaction described in more details below.

Cyclohexylbenzene Oxidation

In order to convert the cyclohexylbenzene into phenol and cyclohexanone, the cyclohexylbenzene is initially oxidized to the corresponding hydroperoxide. This is accomplished by contacting the cyclohexylbenzene with an oxygen-containing gas, such as air and various derivatives of air. For example, it is possible to use air that has been compressed and filtered to removed particulates, air that has been compressed and cooled to condense and remove water, or air that has been enriched in oxygen above the natural approximately 21 mol % in air through membrane enrichment of air, cryogenic separation of air or other conventional means.

Suitable oxidation catalysts include N-hydroxy substituted cyclic imides described in U.S. Pat. No. 6,720,462, which is incorporated herein by reference for this purpose. For example, N-hydroxyphthalimide (NHPI), 4-amino-N-hydroxyphthalimide, 3-amino-N-hydroxyphthalimide, tetrabromo-N-hydroxyphthalimide, tetrachloro-N-hydroxyphthalimide, N-hydroxyhetimide, N-hydroxyhimimide, N-hydroxytrimellitimide, N-hydroxybenzene-1,2,4-tricarboximide, N,N'-dihydroxy(pyromellitic diimide), N,N'-dihydroxy(benzophenone-3,3',4,4'-tetracarboxylic diimide), N-hydroxymaleimide, pyridine-2,3-dicarboximide, N-hydroxysuccinimide, N-hydroxy(tartaric imide), N-hydroxy-5-norbornene-2,3-dicarboximide, exo-N-hydroxy-7-oxabicyclo[2.2.1]hept-5-ene-2,3-dicarboximide, N-hydroxy-cis-cyclohexane-1,2-dicarboximide, N-hydroxy-cis-4-cyclohexene-1,2 dicarboximide, N-hydroxynaphthalimide sodium salt, or N-hydroxy-o-benzenedisulphonimide may be used. Preferably, the catalyst is N-hydroxyphthalimide. Another suitable catalyst is N,N', N"-trihydroxyisocyanuric acid.

These oxidation catalysts can be used either alone or in conjunction with a free radical initiator, and further can be used as liquid-phase, homogeneous catalysts or can be supported on a solid carrier to provide a heterogeneous catalyst. Desirably, the N-hydroxy substituted cyclic imide or the N,N',N"-trihydroxyisocyanuric acid is employed in an amount from 0.0001 wt % to 15 wt %, such as from 0.001 wt % to 5 wt %, of the cyclohexylbenzene.

Suitable conditions for the oxidation step include a temperature from about 70° C. to about 200° C., such as about 90° C. to about 130° C., and a pressure of about 50 kPa to 10,000 kPa. A basic buffering agent may be added to react with acidic by-products that may form during the oxidation. In addition, an aqueous phase may be introduced. The reaction can take place in a batch or continuous flow fashion.

The reactor used for the oxidation reaction may be any type of reactor that allows for introduction of oxygen to cyclohexylbenzene, and may further efficaceously provide contacting of oxygen and cyclohexylbenzene to effect the oxidation reaction. For example, the oxidation reactor may comprise a simple, largely open vessel with a distributor inlet for the oxygen-containing stream. In various embodiments, the oxidation reactor may have means to withdraw and pump a portion of its contents through a suitable cooling device and return the cooled portion to the reactor, thereby managing the exothermicity of the oxidation reaction. Alternatively, cooling coils providing indirect cooling, e.g., by cooling water, may be operated within the oxidation reactor to remove the generated heat. In other embodiments, the oxidation reactor may comprise a plurality of reactors in series, each conducting a portion of the oxidation reaction, optionally operating at different conditions selected to enhance the oxidation reaction at the pertinent conversion range of cyclohexylbenzene or oxygen, or both, in each. The oxidation reactor may be operated in a batch, semi-batch, or continuous flow manner.

Desirably, the product of the cyclohexylbenzene oxidation reaction contains at least 5 wt %, such as at least 10 wt %, for example at least 15 wt %, or at least 20 wt % cyclohexyl-1-phenyl-1-hydroperoxide based upon the total weight of the oxidation reaction effluent. In certain embodiments, the oxidation reaction effluent contains no greater than 80 wt %, or no greater than 60 wt %, or no greater than 40 wt %, or no greater than 30 wt %, or no greater than 25 wt % of cyclohexyl-1-phenyl-1-hydroperoxide based upon the total weight of the oxidation reaction effluent. The oxidation reaction effluent may further comprise imide catalyst and unreacted cyclohexylbenzene. For example, the oxidation reaction effluent may include unreacted cyclohexylbenzene in an amount of at least 50 wt %, or at least 60 wt %, or at least 65 wt %, or at least 70 wt %, or at least 80 wt %, or at least 90 wt %, based upon total weight of the oxidation reaction effluent.

In addition to the desired cyclohexyl-1-phenyl-1-hydroperoxide, the oxidation step tends to produce certain by-products which, if not removed and/or converted to useful materials would result in loss of valuable feed and/or can adversely influence downstream processes. Among these by-products are phenylcyclohexanols, such as of 2-phenyl-1-cyclohexanol, 3-phenyl-1-cyclohexanol, 4-phenyl-1-cyclohexanol, and phenylcyclohexanones, such as 2-phenylcyclohexanone, 3-phenylcyclohexanone, and 4-phenylyclohexanone. Desirably, the phenylcyclohexanols are present in the oxidation reaction effluent in an amount from 0.1 wt % to 10 wt % of the effluent and the phenylcyclohexanones are present in an amount from 0.1 wt % to 5 wt % of the effluent. In the present process, these by-products are removed and converted to useful cyclohexylbenzene, which can then be recycled to the oxidation step. However, as explained below, removal and conversion of these by-products is desirably conducted after the downstream cleavage step.

Hydroperoxide Cleavage

The final reactive step in the conversion of the cyclohexylbenzene into phenol and cyclohexanone involves the acid-catalyzed cleavage of the cyclohexyl-1-phenyl-1-hydroperoxide produced in the oxidation step. Other hydroperoxides that may be present in the oxidation effluent stream may also undergo acid-catalyzed cleavage along with the desired cyclohexyl-1-phenyl-1-hydroperoxide.

In certain embodiments, the acid catalyst used in the cleavage reaction is at least partially soluble in the cleavage effluent, is stable at a temperature of at least 185° C., and has a lower volatility (higher normal boiling point) than cyclohexylbenzene. Desirably, the acid catalyst is also at least partially soluble in the cleavage reaction product. Suitable homogeneous acid catalysts include, but are not limited to, Brønsted acids, Lewis acids, sulfonic acids, perchloric acid, phosphoric acid, hydrochloric acid, p-toluene sulfonic acid, aluminum chloride, oleum, sulfur trioxide, ferric chloride, boron trifluoride, sulfur dioxide and sulfur trioxide. Sulfuric acid is a preferred acid catalyst.

In various embodiments, the cleavage effluent contains at least 50 weight-parts-per-million (wppm) and no greater than 5000 wppm of the acid catalyst, or at least 100 wppm and no greater than 3000 wppm, or at least 150 wppm and no greater than 2000 wppm of the acid catalyst, or at least 300 wppm and no greater than 1500 wppm of the acid catalyst, based upon total weight of the cleavage effluent.

In other embodiments, a heterogeneous acid catalyst is employed for the cleavage reaction, such as molecular sieve, and in particular a molecular sieve having a pore size in excess of 7 Å. Examples of suitable molecular sieves include zeolite beta, zeolite Y, zeolite X, ZSM-12, and mordenite. In one embodiment, the molecular sieve comprises a FAU type zeolite having a unit cell size less than 24.35 Å, such as less than or equal to 24.30 Å, even less than or equal to 24.25 Å. The zeolite can be used in unbound form or can be combined with a binder, such as silica or alumina, such that the overall catalyst (zeolite plus binder) comprises from about 20 wt % to about 80 wt % of the zeolite.

The cleavage reaction mixture may contain a polar solvent, such as an alcohol containing less than 6 carbons, such as methanol, ethanol, iso-propanol, and/or ethylene glycol; a nitrile, such as acetonitrile and/or propionitrile; nitromethane; and a ketone containing 6 carbons or less such as acetone, methylethyl ketone, 2- or 3-pentanone, cyclohexanone, and methylcyclopentanone. The preferred polar solvent is phenol and/or cyclohexanone recycled from the cleavage product after cooling. In certain embodiments, the polar solvent is added to the cleavage reaction mixture such that the weight ratio of the polar solvent to the cyclohexylbenzene hydroperoxide in the mixture is in the range of about 1:100 to about 100:1, such as about 1:20 to about 10:1, and the mixture comprises about 10 wt % to about 40 wt % of the cyclohexylbenzene hydroperoxide. The addition of the polar solvent is found not only to increase the degree of conversion of the cyclohexylbenzene hydroperoxide in the cleavage reaction but also to increase the selectivity of the conversion to phenol and cyclohexanone. Although the mechanism is not fully understood, it is believed that the polar solvent reduces the free radical induced conversion of the cyclohexylbenzene hydroperoxide to undesired products such as hexanophenone and phenylcyclohexanol.

In various embodiments, the cleavage reaction mixture includes cyclohexylbenzene in an amount of at least 50 wt %, or at least 60 wt %, or at least 65 wt %, or at least 70 wt %, or at least 80 wt %, or at least 90 wt %, based upon the total weight of the cleavage reaction mixture.

In certain embodiments, the cleavage reaction is conducted under conditions including a temperature of about 20° C. to about 200° C., such as about 40° C. to about 120° C. and a pressure of about 100 kPa to about 2000 kPa, such as about 100 kPa to about 1000 kPa, such that the cleavage reaction mixture is completely or predominantly in the liquid phase during the cleavage reaction.

The reactor used to effect the cleavage reaction may be any type of reactor known to those skilled in the art. For example, the cleavage reactor may be a simple, largely open vessel operating in a near-continuous stirred tank reactor mode, or a simple, open length of pipe operating in a near-plug flow reactor mode. In other embodiments, the cleavage reactor comprises a plurality of reactors in series, each performing a portion of the conversion reaction, optionally operating in different modes and at different conditions selected to enhance the cleavage reaction at the pertinent conversion range. In one embodiment, the cleavage reactor is a catalytic distillation unit.

In various embodiments, the cleavage reactor is operable to transport a portion of the contents through a cooling device and return the cooled portion to the cleavage reactor, thereby managing the exothermicity of the cleavage reaction. Alternatively, the reactor may be operated adiabatically. In one embodiment, cooling coils operating within the cleavage reactor(s) remove any heat generated.

The major product of the cleavage reaction is desirably a substantially equimolar mixture of phenol and cyclohexanone.

Treatment of Phenylcyclohexanol By-Products

In addition to the desired products, the oxidation and cleavage reactions described above may produce a number of by-products, including phenylcyclohexanols and, in particular, 2-phenyl-1-cyclohexanol, 3-phenyl-1-cyclohexanol, and/or 4-phenyl-1-cyclohexanol. In addition, the 1-phenyl-1-cyclohexanol isomer may also be present in the cleavage effluent if the cleavage does not undergo 100% conversion in the cleavage step. As a result, the cleavage reaction effluent desirably contains from 0.1 wt % to 10 wt %, such as from 0.5 wt % to 5 wt %, of phenylcyclohexanols. In the present process, these phenylcyclohexanols in the cleavage effluent are dehydrated to phenylcyclohexene, and then hydrogenated to cyclohexylbenzene.

However, in some embodiments, the effluent from cleavage reaction will contain residual sulfuric acid cleavage catalyst in addition to the phenol and cyclohexanone products and the phenylcyclohexanol by-products. In this case, the residual sulfuric acid in the cleavage reaction effluent is initially neutralized by treating the cleavage effluent with one or more amines or diamines to produce amine salts. The amine salts are then removed from the neutralized cleavage effluent, desirably by an initial distillation step, with the amine salts being removed as heavies. The remainder of the neutralized cleavage effluent can then be further separated, desirably by a further distillation step, into a light fraction containing phenol and cyclohexanone and a heavy fraction containing the phenylcyclohexanol by-products. The heavy fraction is then fed to a dehydration reaction zone, desirably a fixed bed reactor, for conversion to phenylcyclohexene.

Dehydration of the phenylcyclohexanols to phenylcyclohexene can be effected with high selectivity, high conversion and low catalyst deactivation over a solid acid catalyst comprising a molecular sieve of the MCM-22 family. Preferably, the molecular sieve of the MCM-22 family is MCM-56. The catalyst may also contain an inorganic oxide binder, such as silica, alumina or silica/alumina. In certain embodiments the catalyst does not contain a metal component. The dehydration reaction is desirably conducted at a temperature of 25° C. to 200° C., such as 80° C. to 150° C., a pressure of 15 kPa to 500 kPa and a weight hourly space velocity of 0.1 hr$^{-1}$ to 50 hr$^{-1}$.

The phenylcyclohexene-product of the dehydration reaction may be then supplied together with hydrogen to a hydrogenation reaction zone, which is desirably separate from the dehydration reaction zone and which is conveniently operated at a temperature of 80° C. to 150° C., such as 80° C. to 120° C., and a hydrogen partial pressure of 15 kPa to 1000 kPa, such as 15 kPa to 300 kPa. In certain embodiments, the hydrogenation is conducted in the presence of a catalyst comprising at least one metal selected from Groups 6 to 12 of the Periodic Table of Elements, preferably palladium, on an inorganic support, such as silica. The phenylcyclohexene is thereby converted to cyclohexylbenzene, which can then be recycled to the oxidation stage to enhance the yield of phenol and cyclohexanone.

The dehydration reaction zone and hydrogenation reaction zone can be in separate reactors or in stacked beds in the same reactor.

In some embodiments, it may be desirable to take a vapor or liquid side draw from either the distillation column used to remove the amine salts from the cleavage effluent or from the distillation column used to separate the phenylcyclohexanol by-products and employ this side draw as a feed to the dehydration/hydrogenation reactor. This would also allow integration of the distillation columns with the dehydration/hydrogenation reactor such that the effluent from the reactor could be fed into the distillation column(s) to remove impurities produced in the dehydration/hydrogenation reaction.

The invention will now be more particularly described with reference to the accompanying drawings and the following non-limiting Examples.

Example 1

Comparative

Alcohol Dehydration Using $H_2SO_4$ Catalyst

A first feed solution (Solution A) having the following composition was prepared:

| Component | Amount (gram) | (mole) |
|---|---|---|
| Cyclohexylbenzene | 192.6 | 1.2018 |
| 6-hydroxyhexaphenone | 2.9425 | 0.0153 |
| 4-phenylcyclohexanone | 2.6188 | 0.0150 |
| 1-phenyl-1-cyclohexene | 2.2953 | 0.0145 |
| 4-phenylcyclohexanol | 2.2323 | 0.0127 |
| 2-phenylcyclohexanol | 2.20 | 0.0125 |
| Phenol | 20.25 | 0.215 |
| Cyclohexanone | 20.25 | 0.206 |

5.0 grams of Solution A were added to a round bottom test tube equipped with a magnetic stirrer and different amounts of $H_2SO_4$ (50, 150 and 300 ppm by weight) were added in three separate tests. Each mixture was heated in a silicone oil bath at a temperature of 120° C. and the liquid portion was sampled by Gas Chromatography (GC). FIG. 1 shows the conversion of cyclohexanone in wt % as a function of time on stream (T.O.S.) in minutes, with curves 101, 103 and 105 corresponding to 50 ppm, 150 ppm and 300 ppm of $H_2SO_4$, respectively. The data showed undesirably high conversion of the cyclohexanone product and only low conversion of the phenylcyclohexanols.

Figure 2:
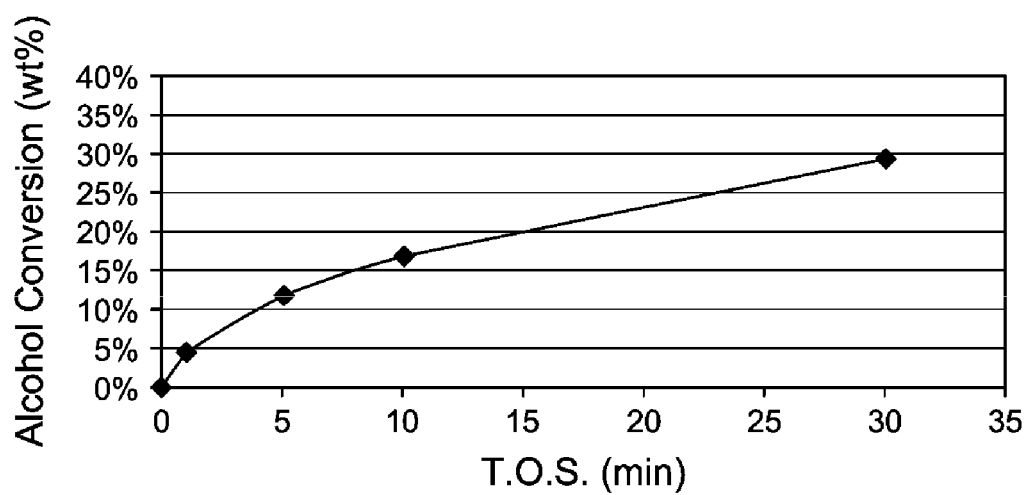
FIG. 2 is a graph comparing alcohol conversion against time on stream for the 500 ppm by weight sulfuric acid concentration used in the process of Example 1.

The process was repeated with a higher concentration of $H_2SO_4$ (500 ppm by weight). The phenylcyclohexanol conversion in wt %, shown in FIG. 2, remained low. Higher cyclohexanone and phenol conversions were also observed.

Example 2

Comparative

Figure 3:
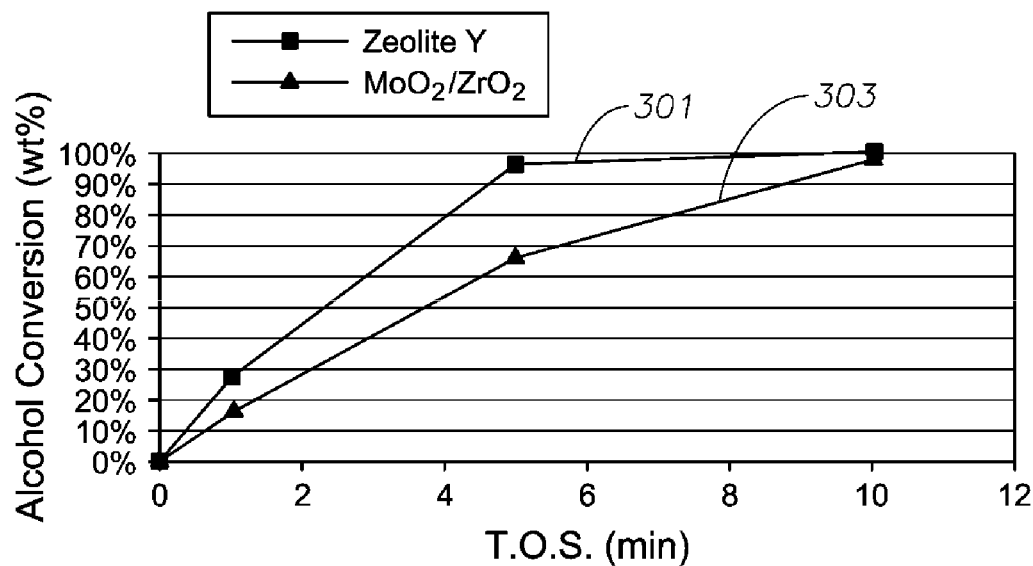
FIG. 3 is a graph comparing alcohol conversion against time on stream for the zeolite Y and $MoO_2/ZrO_2$ catalysts employed in the processes of Examples 2 and 3, respectively.
Figure 4:
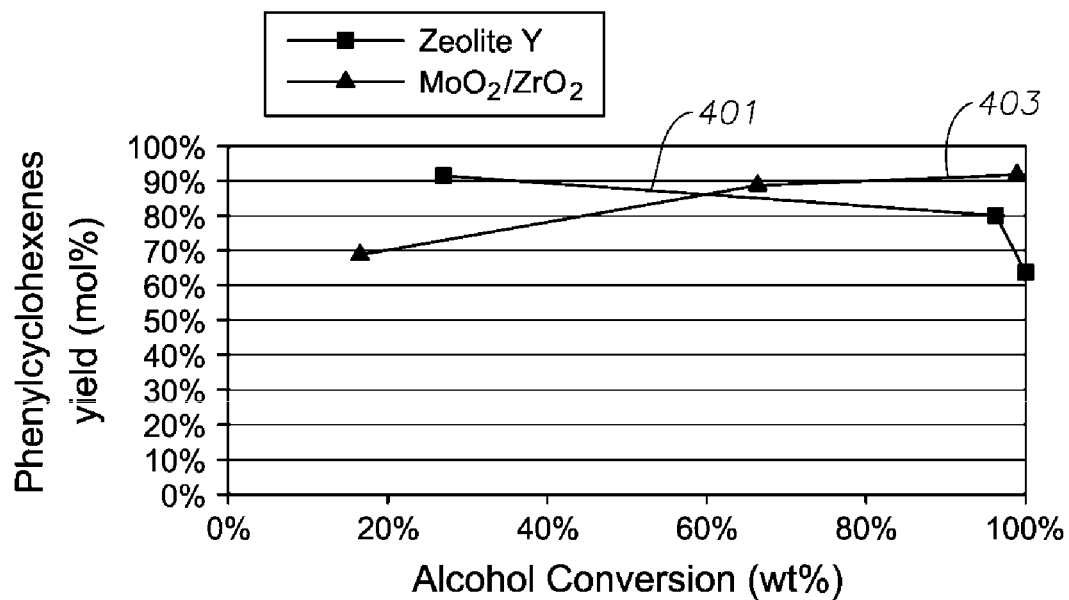
FIG. 4 is a graph comparing phenylcyclohexene yield against alcohol conversion for the zeolite Y and $MoO_2/ZrO_2$ catalysts employed in the processes of Examples 2 and 3, respectively.

Alcohol Dehydration Using Zeolite Y Catalyst 5.0 grams of Solution A were added to a round bottom test tube equipped with a magnetic stirrer, to which 0.5 gram of a powdered zeolite Y catalyst was added. The mixture was heated in a silicone oil bath at a temperature of 120° C. and the liquid portion was sampled by GC. The data are summarized in FIGS. 3 and 4. FIG. 3 shows the conversion of alcohol in wt % as a function of time on stream (T.O.S.) in minutes, where curves 301 and 303 correspond to zeolite Y and $MoO_2/ZrO_2$ (described in Example 3 in detail below) respectively. FIG. 4 shows the yield of phenylcyclohexenes in mol % as a function of conversion of alcohols in wt %, where curves 401 and 403 correspond to zeolite Y and $MoO_2/ZrO_2$ (described in Example 3 in detail below), respectively.

Example 3

Comparative

Alcohol Dehydration Using $MoO_2/ZrO_2$ Catalyst

A $MoO_2/ZrO_2$ catalyst was prepared by initially dissolving 500 grams of $ZrOCl_2.8H_2O$ with stirring in 3.0 liters of distilled water. In addition, a solution containing 260 grams of concentrated $NH_4OH$, 66 grams of $(NH_4)_6Mo_7O_{24}.4H_2O$, and 3.0 liters of distilled water was prepared. Both solutions were heated to 60° C. and the heated solutions were combined at the rate of 50 ml/min using nozzle mixing. The pH of the final composite was adjusted to approximately 9 by the addition of concentrated ammonium hydroxide. The resultant slurry was then put in polypropylene bottles and placed in a steambox (100° C.) for 72 hours. The product formed was recovered by filtration, washed with excess water, and dried overnight at 85° C. A sample of the dried product was calcined to 800° C. in flowing air for 3 hours to produce an acidic oxide catalyst.

5.0 grams of Solution A were added to a round bottom test tube equipped with a magnetic stirrer, to which 0.5 gram of the above prepared $MoO_2/ZrO_2$ catalyst was added. The mixture was heated in a silicone oil bath at a temperature of 150° C. and the liquid portion was sampled by GC. The data are summarized in FIGS. 3 and 4.

The data in FIGS. 3 and 4 show that the zeolite Y catalyst was more reactive than $MoO_2/ZrO_2$ catalyst but, at higher conversion, better selectivity was obtained with the $MoO_2/ZrO_2$ catalyst.

Example 4

Comparative

Figure 5:
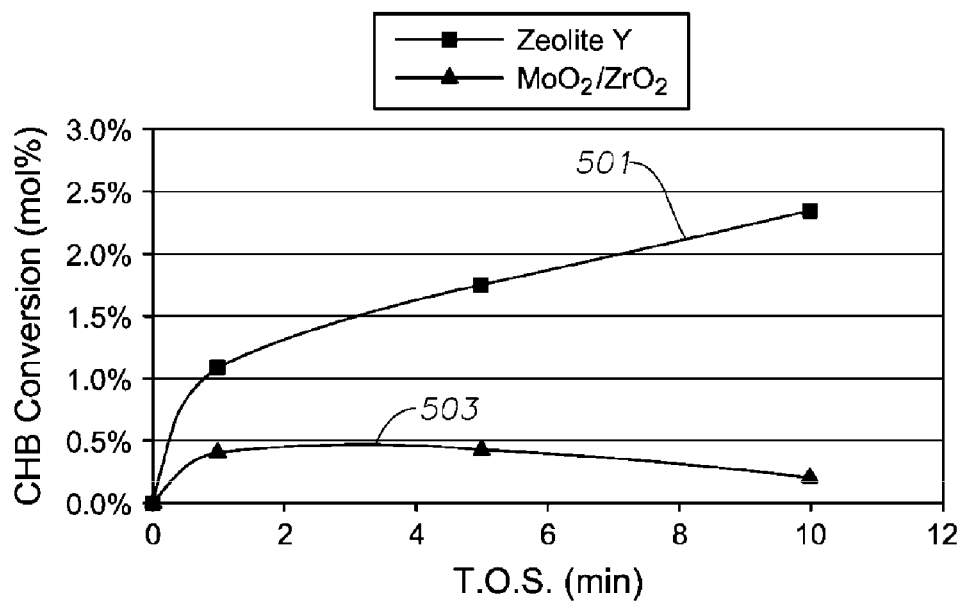
FIG. 5 is a graph comparing cyclohexylbenzene conversion against time on stream for the zeolite Y and $MoO_2/ZrO_2$ catalysts employed in the process of Example 4.

CHB Stability with Zeolite Y And $MoO_2/ZrO_2$ Catalysts 5.0 grams of cyclohexylbenzene were added to a round bottom test tube equipped with a magnetic stirrer and, in one test, 0.5 gram of powdered zeolite Y catalyst was added and, in another test, 0.5 gram of the $MoO_2/ZrO_2$ catalyst of Example 3 was added. Each mixture was heated in a silicone oil bath at a temperature of 120° C. and the liquid portion was sampled by Gas Chromatography (GC). The data is summarized in FIG. 5 and show undesirably high conversion of the cyclohexylbenzene with the zeolite Y catalyst. FIG. 5 shows the cyclohexylbenzene conversion in wt % as a function of time on stream (T.O.S.) in minutes, where curves 501 and 503 correspond to zeolite Y and $MoO_2/ZrO_2$, respectively.

Example 5

Comparative

Alcohol Dehydration Using Fixed Bed Reactor

Into a clean dry ⅜ inch (9.5 mm) (internal diameter) stainless steel tubular reactor was charged 0.5 gram catalyst diluted with 4.5 ml of 20/40 mesh quartz. The ⅜" (9.5 mm) tube was filled with additional 20/40 mesh quartz. The catalyst bed was placed within the heated zone of the fixed bed reactor. In one test, 0.5 gram of powdered zeolite Y catalyst was used and, in another test, 0.5 gram of the $MoO_2/ZrO_2$ catalyst of Example 3 was used.

A second feed solution (Solution B) having the following composition was prepared:

| Component | Amount (gram) | (mole) |
| --- | --- | --- |
| 1,2,4-trimethylbenzene | 988 | 8.22 |
| Pentadecane (Internal Standard) | 87.9 | 0.414 |
| 1-phenyl-1-cyclohexene | 8.0 | 0.051 |
| 6-hydroxylhexaphenone | 4.6 | 0.024 |
| 2-phenyl-1-cyclohexanol | 1.1 | 0.0063 |
| 4-phenyl-1-cyclohexanol | 5.0 | 0.0284 |
| 2-phenylcyclohexanone | 0.94 | 0.0054 |
| 4-phenylcyclohexanone | 4.92 | 0.028 |

Figure 6:
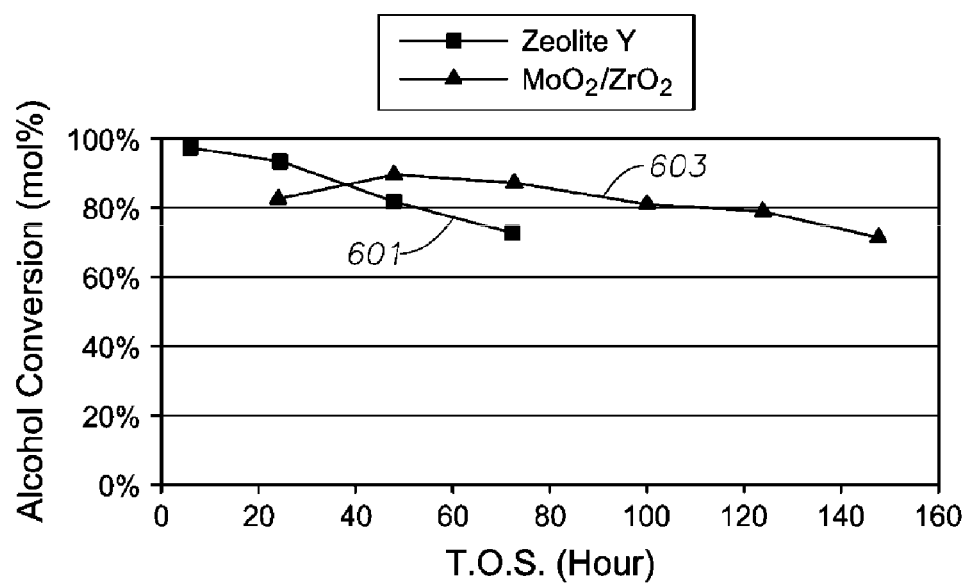
FIG. 6 is a graph comparing alcohol conversion against time on stream for the zeolite Y and $MoO_2/ZrO_2$ catalysts employed in the process of Example 5.
Figure 7:
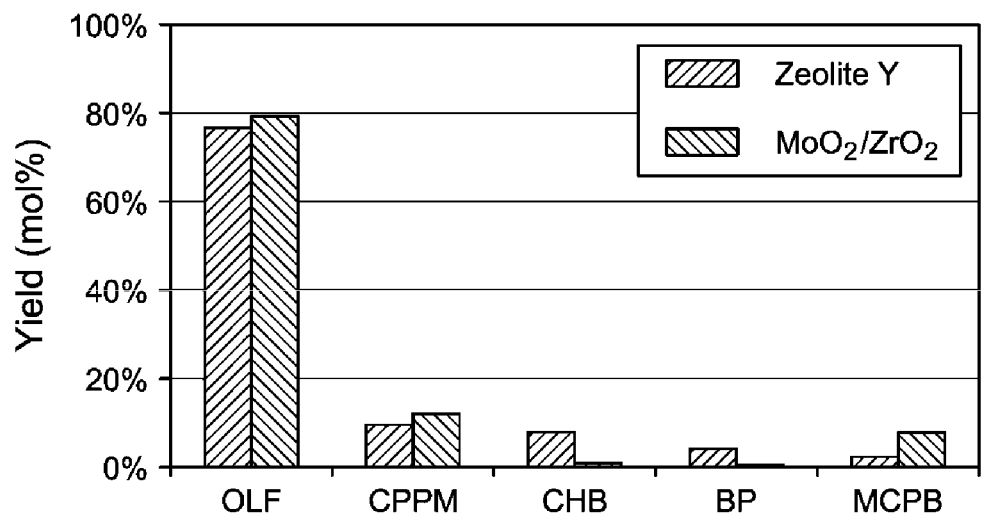
FIG. 7 is a graph showing the yield of different products obtained for the zeolite Y and $MoO_2/ZrO_2$ catalysts employed in the process of Example 5.

Solution B was introduced into the fixed bed reactor at a temperature of 120° C. and a feed rate of 1 cc/hour which corresponds to a WHSV=2. The results are summarized in FIGS. 6 and 7. FIG. 6 shows alcohol conversion in mol % as a function of time on stream (T.O.S.) in minutes. Curves 601 and 603 correspond to zeolite Y and $MoO_2/ZrO_2$, respectively. FIG. 7 shows the yields in mol % of various products, where OLF represents olefins, CMCP represents cyclopentenylmethylbenzene, MCPB represents methylcyclopenentylbenzene, CHB represents cyclohexylbenzene, and BP represents biphenyl. From both figures it can be seen that:

(a) Both catalysts deactivated with the time on stream;
(a) Both catalysts catalyzed ring rearrangement, in that significant quantities of CPMP and MCPB were formed under the reaction conditions; and
(a) Zeolite Y catalyzed hydride transfer to produce biphenyl and cyclohexylbenzene.

Example 6

Inventive

Alcohol Dehydration Using MCM-49 and MCM-56

Figure 8:
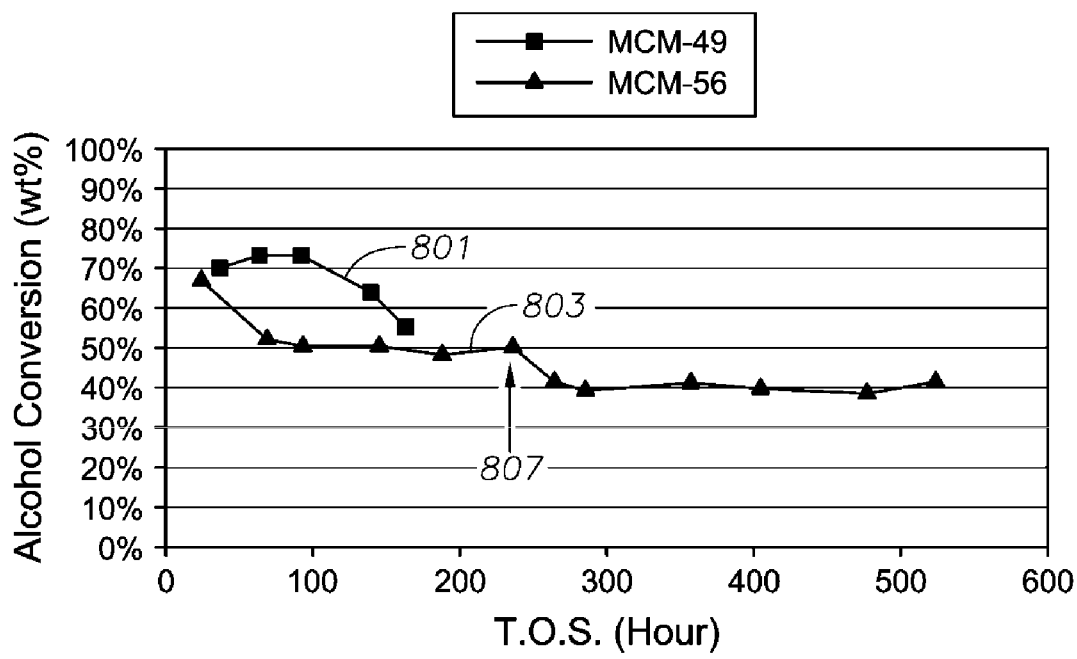
FIG. 8 is a graph comparing alcohol conversion against time on stream for the zeolite MCM-49 and zeolite MCM-56 catalysts employed in the process of Example 6.
Figure 9:
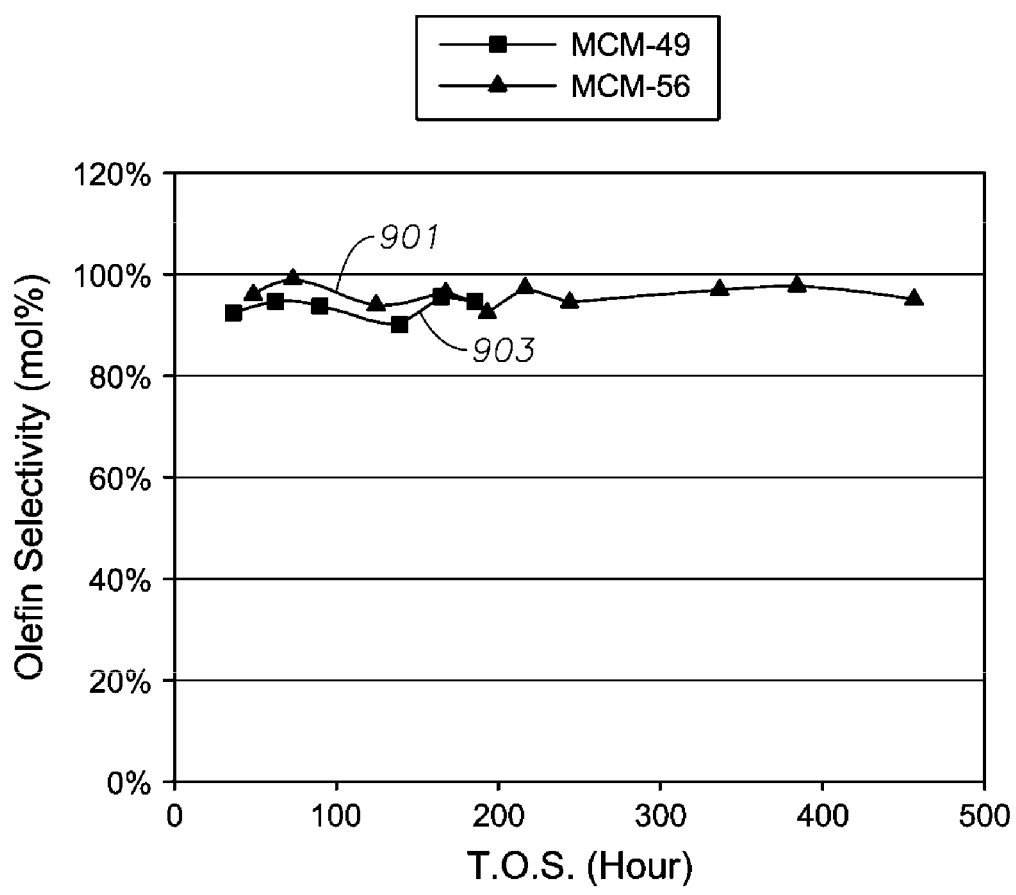
FIG. 9 is a graph comparing olefin selectivity against time on stream for the zeolite MCM-49 and zeolite MCM-56 catalysts employed in the process of Example 6.

The process of Example 5 was repeated with Solution A but with, in one test, 0.5 gram of MCM-49 being used as the catalyst and, in another test, 0.5 gram of MCM-56 being used as the catalyst. The results are summarized in FIGS. 8 and 9. FIG. 8 shows alcohol conversion in wt % as a function of time on stream (T.O.S.) in hours, where curves 801 and 803 correspond to MCM-49 and MCM-56, respectively. Data point 807 corresponds to pump refill. FIG. 9 shows olefin selectivity as a function of time on stream (T.O.S.) in hours, where curves 901 and 903 correspond to MCM-56 and MCM-49, respectively. FIGS. 8 and 9 show that both catalysts are highly selective to the production of phenylcyclohexene and, although MCM-49 is more active than MCM-56, it deactivates faster.

Example 7

Inventive

Alcohol Dehydration Using MCM-56

Figure 10:
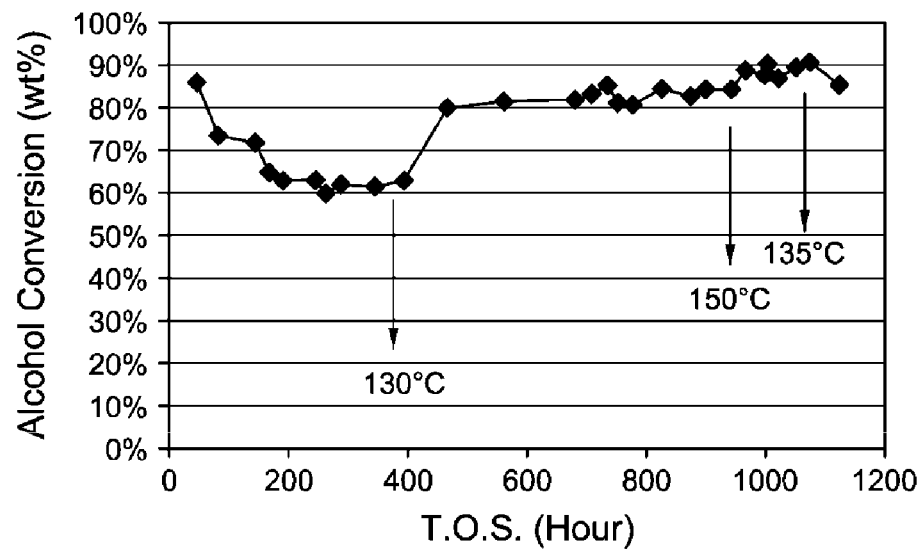
FIG. 10 is a graph comparing alcohol conversion against time on stream for the zeolite MCM-56 catalysts employed in the process of Example 7.
Figure 11:
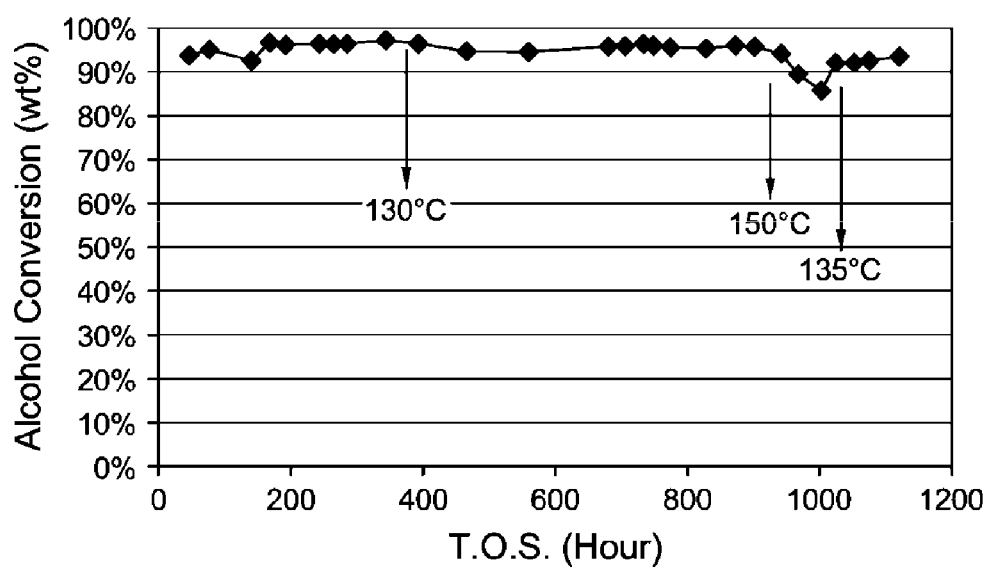
FIG. 11 is a graph comparing olefin selectivity against time on stream for the zeolite MCM-56 catalysts employed in the process of Example 7.

The process of Example 6 was repeated with Solution A and with 0.5 gram of MCM-56 being used as the catalyst but with the temperature being varied from 120° C. to 150° C. over a 1200 hour test. The results are summarized in FIGS. 10 and 11 which show that phenylcyclohexanol dehydration could be performed at high conversion and maintaining high selectivity using the MCM-56 catalyst.

While the present invention has been described and illustrated by reference to particular embodiments, those of ordinary skill in the art will appreciate that the invention lends itself to variations not necessarily illustrated herein. For this reason, then, reference should be made solely to the appended claims for purposes of determining the true scope of the present invention. The contents of all references cited herein are incorporated herein by reference in their entirety.

The invention claimed is:

1. A process for producing phenol and/or cyclohexanone, said process comprising:
   (a) contacting cyclohexylbenzene with an oxygen-containing gas under conditions effective to produce an oxidation effluent containing cyclohexylbenzene hydroperoxide;
   (b) contacting at least part of said oxidation effluent containing cyclohexylbenzene hydroperoxide with a cleavage catalyst under conditions effective to produce a cleavage effluent containing phenol and cyclohexanone,
   wherein at least one of said oxidation effluent and said cleavage effluent contains at least one phenylcyclohexanol as a by-product; and
   (c) contacting at least part of said at least one effluent containing said at least one phenylcyclohexanol with a dehydration catalyst comprising a molecular sieve of the MCM-22 family under conditions effective to convert at least part of said phenylcyclohexanol to phenylcyclohexene.

2. The process of claim 1, wherein said at least one phenylcyclohexanol comprises one or more of 2-phenyl-1-cyclohexanol, 3-phenyl-1-cyclohexanol, and 4-phenyl-1-cyclohexanol.

3. The process of claim 1, wherein said molecular sieve of the MCM-22 family comprises MCM-56.

4. The process of claim 1, wherein said conditions in said contacting step (c) comprise a temperature of 25° C. to 200° C.

5. The process of claim 1, further comprising:
(d) contacting at least part of said phenylcyclohexene produced in said contacting step (c) with hydrogen under conditions effective to convert at least part of said phenylcyclohexene to cyclohexylbenzene and to obtain a hydrogenation effluent.

6. The process of claim 5, wherein said conditions in said contacting step (d) comprise a temperature of 80° C. to 150° C.

7. The process of claim 5, wherein said conditions in said contacting step (d) comprise a hydrogen partial pressure of 15 kPa to 1000 kPa.

8. The process of claim 5, wherein said contacting steps (c) and (d) are conducted in separate reaction zones.

9. The process of claim 5, further comprising:
(e) separating at least part of said cleavage effluent from said contacting step (b) into a first fraction containing phenol and cyclohexanone and a second fraction containing said at least one phenylcyclohexanol; and
(f) supplying said second fraction to said contacting step (c).

10. The process of claim 9, wherein said separating step (e) is effected in a first distillation column.

11. The process of claim 10, wherein said second fraction is removed as a side stream from said first distillation column.

12. The process of claim 10, wherein step (d) is carried out, and at least part of said hydrogenation effluent in said contacting step (d) is fed back to said first distillation column.

13. The process of claim 9, wherein said cleavage catalyst in said contacting step (b) comprises sulfuric acid and said process further comprises:
(g) neutralizing residual sulfuric acid in said cleavage effluent with amines to produce amine salts in said cleavage effluent; and
(h) removing amine salts produced in said cleavage effluent by said neutralizing step (g) prior to said separating step (e).

14. The process of claim 13, wherein said removing step (h) is effected in a second distillation column.

15. The process of claim 5, further comprising:
(i) recycling at least part of said cyclohexylbenzene produced in said contacting step (d) to said contacting step (a).

16. The process of claim 5, wherein said contacting step (a) is effected in the presence of a catalyst.

17. The process of claim 5, wherein said contacting step (a) is effected in the presence of a cyclic imide catalyst.

18. The process of claim 5, wherein said cyclohexylbenzene is produced by alkylation of benzene with cyclohexene.

19. The process of claim 5, wherein said cyclohexylbenzene is produced by reaction of benzene with hydrogen in the presence of a hydroalkylation catalyst.

20. The process of claim 19, wherein said hydroalkylation catalyst comprises an acid alkylation component and a hydrogenating metal component.

21. The process of claim 20, wherein said acid alkylation component comprises a molecular sieve.

22. The process of claim 20, wherein said acid alkylation component comprises a molecular sieve of the MCM-22 family.

23. The process of claim 1, further comprising, prior to the contacting (a):
(a-1) contacting benzene with hydrogen in the presence of a hydroalkylation catalyst under a hydroalkylation condition effective to produce a hydroalkylation effluent comprising said cyclohexylbenzene contacted with the oxygen-containing gas in (a).

24. The process of claim 23, further comprising:
(d) contacting at least part of said phenylcyclohexene produced in said contacting step (c) with hydrogen under conditions effective to convert at least part of said phenylcyclohexene to cyclohexylbenzene and to obtain a hydrogenation effluent.

25. The process of claim 24, further comprising:
(e) separating at least part of said cleavage effluent from said contacting step (b) into a first fraction containing phenol and cyclohexanone and a second fraction containing said at least one phenylcyclohexanol; and
(f) supplying said second fraction to said contacting step (c).

* * * * *